US006245747B1

(12) United States Patent
Porter et al.

(10) Patent No.: US 6,245,747 B1
(45) Date of Patent: Jun. 12, 2001

(54) TARGETED SITE SPECIFIC ANTISENSE OLIGODEOXYNUCLEOTIDE DELIVERY METHOD

(75) Inventors: Thomas R. Porter; Patrick L. Iversen, both of Omaha, NE (US); Gary D. Meyer, Athens, OH (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/114,399

(22) Filed: Jul. 13, 1998

Related U.S. Application Data (63) Continuation-in-part of application No. 08/615,495, filed on Mar. 12, 1996, now abandoned.

(51) Int. Cl.$^7$ .......................... A01N 43/04; A61K 31/70; A61K 49/00; C12N 15/00; C12N 13/00
(52) U.S. Cl. .................. 514/44; 435/455; 435/320.1; 435/173.1; 424/9.5; 424/9.52; 536/24.31
(58) Field of Search .................. 514/44; 435/455, 435/320.1, 173.1; 424/9.5, 9.52; 536/24.31

(56) References Cited

U.S. PATENT DOCUMENTS

| | | |
|---|---|---|
| 4,572,203 | 2/1986 | Feinstein . |
| 4,634,586 | 1/1987 | Goodwin et al. ............ 424/1.1 |
| 4,718,433 | 1/1988 | Feinstein . |
| 4,774,958 | 10/1988 | Feinstein . |
| 4,844,882 | 7/1989 | Widder et al. . |
| 4,957,656 | 9/1990 | Cerny et al. . |
| 5,040,537 | 8/1991 | Katakura . |
| 5,107,842 | 4/1992 | Levene et al. . |
| 5,255,683 | 10/1993 | Monaghan . |
| 5,304,325 | 4/1994 | Kaufman et al. . |
| 5,310,540 | 5/1994 | Giddey et al. . |
| 5,315,997 | 5/1994 | Widder et al. . |
| 5,315,998 | 5/1994 | Tachibana et al. . |
| 5,380,519 | 1/1995 | Schneider et al. . |
| 5,385,147 | 1/1995 | Anderson et al. . |
| 5,385,725 | 1/1995 | Lin et al. . |
| 5,393,524 | 2/1995 | Quay . |
| 5,401,493 | 3/1995 | Lohrmann et al. . |
| 5,409,688 | 4/1995 | Quay . |
| 5,410,516 | 4/1995 | Uhlendorf et al. . |
| 5,413,774 | 5/1995 | Schneider et al. . |
| 5,439,686 | 8/1995 | Desai et al. . |
| 5,445,813 | 8/1995 | Schneider et al. . |
| 5,512,268 | 4/1996 | Grinstaff et al. . |
| 5,540,909 | 7/1996 | Schutt . |
| 5,542,935 | 8/1996 | Unger et al. . |
| 5,552,133 | 9/1996 | Lambert et al. . |
| 5,558,853 | 9/1996 | Quay . |
| 5,560,364 | 10/1996 | Porter . |
| 5,567,415 | 10/1996 | Porter . |
| 5,580,859 | 12/1996 | Felgner et al. . |
| 5,585,479 | 12/1996 | Hoke et al. ............ 536/24.5 |
| 5,770,222 | * 6/1998 | Unger et al. ............ 424/450 |

FOREIGN PATENT DOCUMENTS

| | | | |
|---|---|---|---|
| 0633 030 A1 | 1/1985 | (EP) | .............. A61K/49/00 |
| WO 92/05806 | 3/1992 | (WO) | .............. A61K/49/00 |
| WO 93/05819 | 4/1993 | (WO) | .............. A61K/49/00 |
| WO 94/16739 | 8/1994 | (WO) | .............. A61K/49/00 |
| WO 95/23615 | 9/1995 | (WO) | .............. A61K/49/00 |
| WO 98/00172 | 1/1998 | (WO) . | |
| WO 98/18498 | 5/1998 | (WO) . | |

OTHER PUBLICATIONS

Porter et al., Journal of Ultrasound Medicine, vol. 15, pp. 577–584, Aug. 1996.*
Anderson, Editorial, "Gene Therapy for Genetic Diseases", *Human Gene Therapy*, vol. 5, pp. 281–282 (1994), Mary Ann Liebert, Inc., Publishers.
Applied Pharmacokinetics, Principles of Therapeutic Drug Monitoring, Third Edition (1992), Applied Therapeutics, Inc., Vancouver, WA, Chapter 5: Influence of Protein Binding (1992), William E. Evans editor.
Bleeker, H., "On the Application of Ultrasonic Contrast Agents for Blood Flowmetry and Assessment of Cardiac Perfusion", *Ultrasound Med*, 9:461–471 (1990).
Brown, "New Media, Researchers 'Oversold' Gene Therapy, Advisory Panel Says", The Washington Post (Dec. 8, 1995).
Challita & Kohn, "Lack of Expression from a Retroviral Vector After Transduction of Murine Hematopoietic Stem Cells is Associated with Methylation in vivo", *Proc. Natl. Acad. Sci., USA*, vol. 91, pp. 2567–2571 (Mar. 1994).
Coghlan, Focus, Editorial, "Gene Dream Fades Away", *New Scientist*, vol. 148, No. 2005, pp. 14–15 (Nov. 25, 1995).
Gura, T., "Antisense Has Growing Pains", *Science*, vol. 270, pp. 575–577 (1995).
Jaroff, "Keys to the Kingdom", *Time*, vol. 148, No. 14, pp. 25–29 (1996).
Kricsfeld, A., "Detection of Regional Perfusion Abnormalities During Adenoosine Stress Echocardiography Using Intravenous Perfluoropropane–enhanced Sonicated Dextrose Albumin", *J. Am. Col. of Card.*, special issue, p. 38A Feb. 1995 (abstract XP000577057).

*Primary Examiner*—Jill D. Martin
(74) *Attorney, Agent, or Firm*—Heidi S. Nebel; LeeAnn Gorthey (57) ABSTRACT

The invention relates to a new and improved pharmaceutical composition and method for delivery of therapeutic agents. The methods and composition of the invention can be used with several therapeutic agents and can achieve site specific delivery of a therapeutic substance. This can allow for lower doses and for improved efficacy with drugs which traditionally reach targeted sites and can result in utility for agents such as oligonucleotides which are plagued with problems in reaching targeted sites in necessary therapeutic levels.

The delivery system includes gas-filled microbubbles formed in a nitrogen-free environment. Microbubbles formed through sonication in a nitrogen-free environment are smaller and more stable than microbubbles sonicated in the presence of room air.

6 Claims, 1 Drawing Sheet

OTHER PUBLICATIONS

Marshall, "Gene Therapy's Growing Pains", *Science*, vol. 269, pp. 1050–1055 (Aug. 25, 1995).

Orkin et al., Report and Recommendations of the Panel to Assess the NIH Investment in Research on Gene Therapy (Dec. 7, 1995).

Porter et al., "The Mechanism and Clinical Implication of Improved Left Ventricular Videointensity Following Intravenous Injection of Multi–fold Dilutions of Albumin with Dextrose", *International Journal of Cardiac Imaging*, vol. 11, pp. 117–125 (1995).

Porter et al., "Transient Myocardial Contrast After Initial Exposure to Diagnostic Ultrasound Pressures with Minute Doses of Intravenously Injected Microbubbles: Demonstration and Potential Mechanisms", *Circulation*, vol. 92, No. 9, pp. 2391–2395 (1995).

Porter, T., "Echocardiographic Detection of Residual Coronary Flow Abnormalities and Stenosis Severity After Coronary Reperfusion Using Intravenous Perfluoropropane–enhanced Sonicated Dextrose Albumin", 44th Annual Scientific Session of the American College of Cardiology, New Orleans, LA, USA, March 19–22, 1995, *J. Am. Col. of Card.*, special issue, p. 205A Feb. 1995 (abstract 95–60) XP000577058.

Porter, T., "Multifold Sonicated Dilutions of Albumin With Fifty Percent Dextrose Improve Left Ventricular Contrast Videointensity After Intravenous Injection in Human Beings", *J. Am. Soc. Echocard.*, 7(5) 465–471 (1994).

Porter, T., "Myocardial Contrast Echocardiography for the Assessment of Coronary Blood Flow Reserve: Validation in Humans", *JACC*, 21(2) 349–355 (1993).

Porter, T., "Noninvasive Indentification of Acute Myocardial Ischemia and Reperfusion with Contrast Ultrasound Using Intravenous Perfluoropropane–Exposed Sonicated Dextrose Albumin", *J. Am. Col. of Card.*, 26(1) 33–40 (1995).

Porter, T., "Visually Discernible Myocardial Echocardiographic Contrast After Intravenous Injection of Sonicated Dextrose Albumin Microbubbles Containing High Molecular Weight, Less Soluble Gases", *J. Am. Col. of Card.*, 25(2) 509–515 (1995).

Putterman, S., "Sonoluminescence: Sound into Light", Feb. 1995, *Scientific American*, 46–51.

Srinivasan, Shashi Kumar "Characterization of Binding Sites, Extent of Binding, and Drug Interactions of Oligonucleotides with Albumin", *Antisense Research and Development* 5:131–139 (1995).

Xie, F., "Acute Myocardial Ischemia and Reperfusion can be Visually Identified Non–invasively with Intravenous Perfluoropropane–Enhanced Sonicated Dextrose Albumin Ultrasound Contrast", *Abstract From the 67th Scientific Sessions Dallas Convention Center*, Dallas TX, Nov. 14–17, 1994) 90(2) Part 2, p. 1555 Oct. 1994 (abstract XP000577054).

Xie, F., "Perfluoropropane Enhanced Sonicated Dextrose Albumin Produces Visually Apparent Consistent Myocardial Opecification with Physiologic Washout and Minimal Homodynamic Changes Following . . . Injection", *Abstract From the 67th Scientific Sessions Dallas Convention Center*, Dallas TX, Nov. 14–17, 1994) 90(4) Part 2, p.269 Oct. 1994 (abstract XP000577055).

Porter, T.R., et al., "The Effect of Microbubble Gas Composition and External Ultrasound Frequency on the Non–Invasive Enhancement of Antisense Oligonucleotide Delivery to the Vascular Wall in Pigs" *Circulation*, US, Dallas, TX 96(8) :L–401 #2249.

* cited by examiner

Fig. 1

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: PS-ODN

<400> SEQUENCE: 1
aacgttgagg ggcat                                             15
```

-continued

```
<210> SEQ ID NO 2
<211> LENGTH: 24
<212> TYPE: DNA
<213> ORGANISM: Artificial Sequence
<220> FEATURE:
<223> OTHER INFORMATION: PS-ODN

<400> SEQUENCE: 2
tatgctgtgc cggggtcttc gggc                                              24

<210> SEQ ID NO 3
<211> LENGTH: 6
<212> TYPE: DNA
<213> ORGANISM: Artificial Sequence
<220> FEATURE:
<223> OTHER INFORMATION: PS-ODN

<400> SEQUENCE: 3 ttaggg                                                                   6

<210> SEQ ID NO 4
<211> LENGTH: 20
<212> TYPE: DNA
<213> ORGANISM: Artificial Sequence
<220> FEATURE:
<223> OTHER INFORMATION: PS-ODN

<400> SEQUENCE: 4
ccctgctccc ccctggctcc                                                   20
```

TARGETED SITE SPECIFIC ANTISENSE OLIGODEOXYNUCLEOTIDE DELIVERY METHOD

CROSS-REFERENCE TO RELATED APPLICATION

This application is a continuation-in-part of application Ser. No. 08/615,495, filed Mar. 12, 1996, now abandoned, the disclosure of which is hereby incorporated by reference.

FIELD OF THE INVENTION

This invention relates to a new and improved pharmaceutical composition and method for delivery of bioactive substances. The methods and composition of the invention can be used with several agents and can achieve site specific delivery of a biologically active substance. This can allow for lower doses and for improved efficacy with drugs particularly agents such as oligonucleotides which are plagued with problems in achieving therapeutic concentrations in targeted organs.

BACKGROUND OF THE INVENTION

Drug delivery techniques are employed in the formulation of all drug therapy to augment drug availability, to reduce drug dose, and consequently to reduce drug-induced side effects. These techniques serve to control, regulate, and target the release of drugs in the body. The goals have been to provide less frequent drug administration, to maintain constant and continuous therapeutic levels of a drug in the systemic circulation or at a specific target organ site, to achieve a reduction in undesirable side effects, and to promote a reduction in the amount and dose concentration required to realize the desired therapeutic benefits. Finally, a method to noninvasively target the delivery of a desired drug to a target organ is needed.

To date, drug delivery systems have included drug carriers based upon proteins, polysaccharides, synthetic polymers, erythrocytes, DNA and liposomes. New generation biologicals such as monoclonal antibodies, gene therapy vectors, anti-cancer drugs such as taxol, viral based drugs, and oligonucleotides (ODN) and poly nucleotides have presented several problems with regard to delivery. In fact drug delivery may be the primary hurdle to achieving mainstream therapeutic use of these agents whose initial potential seemed unlimited but whose therapeutic parameters have prevented realization of full benefit.

Synthetic oligodeoxyribonucleotides (ODN's) which are chemically modified to confer nuclease resistance represent a fundamentally different approach to drug therapy. The most common applications to date are antisense ODN's with sequences complementary to a specific targeted MRNA sequence. An antisense oligonucleotide approach to therapy involves a remarkably simple and specific drug design concept in which the ODN causes a mechanistic intervention in the processes of translation or an earlier processing event. The advantage of this approach is the potential for gene-specific actions which should be reflected in a relatively low dose and minimal non-targeted side effects.

Phosphorothioate analogs of polynucleotides have chiral internucleoside linkages in which one of the non-bridging ligands is sulfur. The phosphorothioate analog is currently the most commonly employed analogue in biological studies including both in vitro and in vivo. The most apparent disadvantages of phosphorothioate oligonucleotides include the high cost of preparation of sufficient amounts of high quality material and non-specific binding to proteins. Hence, the primary advantages of the antisense approach (low dose and minimal side effects) fall short of expectations.

Drug delivery efforts with regard to oligonucleotides and polynucleotides have focused on two key challenges; transfection of oligonucleotides into cells and alteration of distribution of oligonucleotides in vivo.

Transfection involves the enhancement of in vitro cellular uptake. Biological approaches to improve uptake have included viral vectors such as reconstituted viruses and pseudovirions, and chemicals such as liposomes. Methods to improve biodistribution have focused on such things as cationic lipids, which are postulated to increase cellular uptake of drugs due to the positively charged lipid attraction to the negatively charged surfaces of most cells.

Lipofection and DC-cholesterol liposomes have been reported to enhance gene transfer into vascular cells in vivo when administered by catheter. Cationic lipid DNA complexes have also been reported to result in effective gene transfer into mouse lungs after intratracheal administration.

Cationic liposomal delivery of oligonucleotides has also been accomplished, however, altered distribution to the lung and liver was experienced. Asialoglycoprotein poly(L)-lysine complexes have met with limited success as well as complexation with Sendai virus coat protein containing liposomes. Toxicity and biodistribution, however, have remained significant issues.

From the foregoing it can be seen that a targeted drug delivery system for delivery of biologics, particularly poly and oligo nucleotides is needed for these drugs to achieve their fullest potential.

One object of this invention is to provide a novel composition of matter to deliver a pharmaceutical agent to a targeted site in vivo.

Another object of the invention is to provide a method for delivering a pharmaceutical agent to a specific site with the use of low frequency ultrasound.

Another object of the invention is to provide a method of enhancing the effectiveness of currently available drugs including plasma-bound drugs with the use of albumin or orosomucoid-albumin perfluorocarbon containing microbubbles when combined with diagnostic ultrasound.

Another object of the invention is to provide a method of enhancing the stability and decreasing the size of perfluorocarbon containing microbubbles by sonicating them in a nitrogen-free environment.

Other objects of the inventions will become apparent from the description of the invention which follows.

SUMMARY OF THE INVENTION

According to the invention a new biologically active agent delivery method and composition are disclosed. The compositions and methods can be used to deliver agents such as therapeutics or diagnostics which have been plagued with delivery problems such as oligonucleotides as well as traditional agents and can drastically reduce the effective dosages of each, increasing the therapeutic index and improving bioavailability. This in turn can reduce drug cytotoxicity and side effects. Furthermore, this invention can enhance the effectiveness of other plasma-bound drugs such as heparin, diltiazem, lidocaine, propanolol, cyclosporine, and chemotherapeutic agents which require blood pool activation. For example, applicants have shown that the anticoagulant properties of heparin can be dramatically enhanced by first combining the medicament with orosomucoid-labeled perfluorocarbon exposed sonicated dextrose albumin, and then given the combination intravenously.

The invention employs equilibrium binding of the biologic agent with a filmogenic protein which is formed as a protein shell microbubble encapsulating an insoluble gas. The conjugates are designed for parenteral administration as an aqueous suspension. After administration and timed with travel of the injected bolus to the site of interest, energy administered in the form of sound waves causes the microbubbles to cavitate; the agent is then released and concomitantly delivered to the organ or other site or interest.

Improved gas-filled microbubbles are achieved by forming the microbubbles in the presence of a nitrogen-free environment. The nitrogen-free environment makes microbubbles which are smaller but more stable in venous and arterial blood. These smaller microbubbles produce greater diagnostic ultrasound contrast in the myocardium and therefore can carry drugs to these regions with greater efficacy in therapeutic embodiments.

DESCRIPTION OF THE FIGURES

FIG. 1 is a Lineweaver-Burke plot of the binding data for PESDA microbubbles with PS-ODN. The equilibrium dissociation constant $K_m$ (calculated for the 7 concentrations which were run in duplicate) for the binding to the microbubbles was $1.76\times10^{-5}$M. This is nearly within the range observed for binding a 15mer PS-ODN with sequence 5'd(AACGTTGAGGGGCAT)-3' SEQ ID NO:1 to human serum albumin in solution of 3.7–4.8×10–5M previously reported Srinivasan SK et al, "Characterization of binding sites, extent of binding, and drug interactions of oligonucleotides with albumin. *Antisense Res. Devel.* 5:131, 1995.

DETAILED DESCRIPTION OF THE INVENTION

Ultrasonic imaging has long been used as a diagnostic tool to aid in therapeutic procedures. It is based on the principle that waves of sound energy can be focused upon an area of interest and reflected to produce an image. Generally an ultrasonic transducer is placed on a body surface overlying the area to be imaged and ultrasonic energy, produced by generating and receiving sound waves, is transmitted. The ultrasonic energy is reflected back to the transducer where it is translated into an ultrasonic image. The amount and characteristics of the reflected energy depend upon the acoustic properties of the tissues, and contrast agents which are echogenic are preferably used to create ultrasonic energy in the area of interest and improve the imaging received. For a discussion of contrast echographic instrumentation, see, DeJong and, "Acoustic Properties of Ultrasound Contrast Agents", CIP-GEGEVENS KONINKLIJKE BIBLIOTHEEK, DENHAG (1993), pp. 120 et seq.

Contrast echocardiography has been used to delineate intracardiac structures, assess valvular competence, and demonstrate intracardiac shunts. Myocardial contrast echocardiography (MCE) has been used to measure coronary blood flow reserve in humans. MCE has been found to be a safe and useful technique for evaluating relative changes in myocardial perfusion and delineating areas at risk.

Ultrasonic vibration has also been used at therapeutic levels in the medical field to increase the absorption of various medicaments. For example in Japanese Patent Kokai number 115591/1977 discloses that percutaneous absorption of a medicament is enhanced by ultrasonic vibration. U.S. Pat. Nos. 4,953,565 and 5,007,438 also disclose a technique of percutaneous absorption of medicaments by the aid of ultrasonic vibration. U.S. Pat. No. 5,315,998 discloses a booster for drug therapy comprising microbubbles in combination ultrasonic energy to allow the medicament to diffuse and penetrate. This discloses the use of therapeutic levels of ultrasound for up to 20 minutes in contrast to the present invention which uses diagnostic levels of ultrasound with exposure for much shorter time periods to achieve release of conjugated bioactive agents.

Applicant has demonstrated that traditional diagnostic ultrasound therapy (e.g. including peak negative pressures in the range of 0.1 to 3.5 Megapascals, and transmit frequencies in the range of 1.0 to 40 Megahertz) and contrast agents can be used as a specific targeted delivery application to release therapeutic agents at the exact site of interest. In a preferred embodiment low frequency ultrasound is used, namely frequencies less than 1 megahertz, most preferably from about 10 kilohertz to about 40 kilohertz.

In the presence of ultrasound the microbubbles cavitate and release conjugated bioactive agents and thus delivers them to the target site.

The pharmaceutical composition of the invention comprises a liquid suspension containing microbubbles of an insoluble gas having a diameter of 0.1 to 10 microns. The microbubbles are formed by entrapping microbubbles of a gas into a liquid. The microbubbles are made of various insoluble gases such as fluorocarbons or sulfur hexafluoride gas. The liquid includes any liquid which can form microbubbles. Generally any insoluble gas can be used. It must be gaseous at body temperature and be nontoxic. The gas must also form stable microbubbles of average size of between about 0.1 and 10 microns in diameter when the pharmaceutical composition is sonicated to form microbubbles. Generally perfluorocarbon gases such as perfluoromethane, perfluoroethane, perfluoropropane, perfluorobutane, and perfluoropentane are preferred. Of these gases, perfluoropropane and perfluorobutane are especially preferred because of their demonstrated safety for intraocular injection in humans. They have been used in human studies for intraocular injections to stabilize retinal detachments (Wong and Thompson, Opthamology 95:609–613). Treatment with intraocular perfluoropropane is considered to be the standard of care for treatment of this disorder. The gases must also have a diffusion coefficient and blood solubility lower than nitrogen or oxygen which diffuse once in the internal atmosphere of the blood vessel.

Other inert gases such as sulfur hexafluoride are also useful in the invention provided they have a diffusion coefficient and blood solubility lower than nitrogen or oxygen. The agent of the invention is formulated in a pharmaceutically effective dosage form for peripheral administration to the host in conjunction with ultrasound therapy. Generally such host is a human host, although other mammalian hosts such as canine or equine can also be subject to this therapy.

The pharmaceutical liquid composition of the invention uses a liquid wherein the gaseous microbubbles are stabilized by a filmogenic protein coating. Suitable proteins include naturally occurring proteins such as albumin, human gamma globulin, human apotransferrin, Beta lactose and urease. The invention preferably employs a naturally occurring protein but synthetic proteins may also be used. Particularly preferred is human serum albumin.

It is also preferred to use an aqueous solution containing a mixture of a pharmaceutically accepted saccharide e.g., dextrose, in combination with the earlier described protein. In a most preferred embodiment the pharmaceutical liquid composition of the invention is the sonicated mixture of commercially available albumin (human), U.S.P. solution (generally supplied as 5% or 25% by weight sterile aqueous solutions), and commercially available dextrose, U.S.P. for intravenous administration. The mixture is sonicated under ambient conditions i.e. room air temperature and pressure and is perfused with an insoluble gas (99.9% by weight) during sonication.

In a most preferred embodiment the pharmaceutical liquid composition includes a two-fold to eight-fold dilution of 5% to 50% by weight of dextrose and a 2% to 10% by weight of human serum albumin. Exemplary of other saccharide solutions of the invention are aqueous monosaccharide solution (e.g. having the formula $C_6H_{12}O_6$ such as the hexose sugars, dextrose or fructose or mixtures thereof), aqueous disaccharide solution (e.g. having a formula $C_{12}H_{22}O_{11}$ such as sucrose, lactose or maltose or mixtures thereof), or aqueous polysaccharide solution (e.g. soluble starches having the formula $C_6H_{10}O_5(n)$ wherein n is a whole number integer between 20 and about 200 such as amylase or dextran or mixtures thereof. The saccharide, however is not essential to achieve the results of the invention.

The microbubbles are formed by sonication, typically with a sonicating horn. Sonication by ultrasonic energy causes cavitation within the dextrose albumin solution at sites of particulate matter or gas in the fluid. These cavitation sites eventually resonate and produce small microbubbles (about 7 microns in size) which are non-collapsing and stable. In general, sonication conditions which produce concentrations of greater than about $4\times10^8$ m of between about 5 and about 6 micron microbubbles are preferred. Generally the mixture will be sonicated for about 80 seconds, while being perfused with the insoluble gas.

A second method of preparation includes hand agitating 15±2 ml of sonicated dextrose albumin with 8±2 ml of perfluorocarbon gas prior to sonication. Sonication then proceeds for 80±5 seconds.

A third method of preparation, designed to improve the affinity of the microbubble for many plasma-bound drugs, is to add 5 to 30 milligrams of orosomucoid (alpha-acid glycoprotein) to the albumin-dextrose prior to sonication.

In a preferred embodiment, the microbubbles are formed in a nitrogen-free environment. Microbubbles formed in a nitrogen-free environment are significantly smaller than those formed in the presence of room air. These smaller microbubbles are more stable and result in improved delivery of therapeutics and diagnostics.

The inventors became aware of the advantages of using a nitrogen-free environment through the observation that gas-filled microbubbles produced better ultrasound contrast following venous injection than room air filled microbubbles. One reason for this improved contrast is the prolonged survival of the gas-filled microbubbles following intravenous injection. In comparison, room air filled microbubbles of comparable size are rapidly destroyed following venous injection because of rapid diffusion of the soluble gases out of the microbubble. Computer simulations, however, have shown that these soluble gases still affect the size of gas-filled microbubbles in blood, thereby affecting their ultrasound characteristics. Burkard, M. E. et al. (1994), Oxygen transport to tissue by persistent bubbles: theory and simulations. *J Appl Physiol* 2874–8. These models have theorized that blood nitrogen plays an important role in preventing the outward diffusion of the gas within the microbubble.

It was postulated that by enhancing microbubble oxygen content (thus lowering partial pressures of nitrogen within the microbubble), they could prolong microbubble survival in blood. The presence of a nitrogen-free environment was found to produce substantially smaller microbubbles which are more stable in the bloodstream. This results in improved contrast and drug delivery.

These microbubble sizes are particularly ideal since a microbubble must have a mean diameter of less than 10 microns and greater than 0.1 to be sufficient for transpulmonary passage, and must be stable enough to prevent significant diffusion of gases within the microbubble following intravenous injection and during transit to the target site. As used herein the term "nitrogen free" shall mean a nitrogen content which is less than that of room air such that the partial pressure of nitrogen in the gas-filled microbubbles formed by sonication is lower than that achieved from sonication in the presence of room air (typically about 70–80% nitrogen).

The microbubbles are next incubated with the biologically active agent so that the medicament becomes conjugated with the protein coated microbubble. Quite unexpectedly applicant has demonstrated that filmogenic proteins in the form of microbubbles, as previously used in contrast agents, retain their ability to bind compounds, when the microbubbles are filled with an insoluble gas. This is surprising because traditionally it was thought that in the formation of microbubble contrast agents the protein sphere was comprised of denatured protein. For example see U.S. Pat. Nos. 4,572,203, 4,718,433 and 4,774,958, the contents of each of which are incorporated herein by reference. As demonstrated herein, applicant has shown that when an insoluble gas instead of air is used for the microbubble, much of the sonication energy is absorbed by the gas and the protein retains its binding activity. Thus the protein, such as albumin, can bind to biologically active medicaments to form a microbubble agent conjugation. Air filled microbubbles do not retain their binding capabilities and cannot be used in the method of the invention.

The therapy involves the use of a pharmaceutical composition conjugated to protein microbubbles of a diameter of about 0.1 to 10 microns. The invention uses agents and methods traditionally used in diagnostic ultrasound imaging and as such provides a means for visualization of the therapeutic at its target site for delivery of the therapeutic.

Therapeutic agents useful in the present invention are selected via their ability to bind with the filmogenic protein. For example if the filmogenic protein is albumin, the therapeutic can include oligonucleotides, polynucleotides, or ribozymes all of which can bind with albumin and as such can form a conjugation with the microbubble. A list of drugs which bind to albumin at site 1 which is confirmed to remain intact and thus would be useful in the methods and compositions of the present invention with albumin coated microbubbles follows:

| Drug | % Albumin Binding | Drug Class |
|---|---|---|
| Naproxen | 99.7 | NSAID⊕ |
| Piroxicam | 99.3 | NSAID⊕ |
| Warfarin | 99.0 | Anticoagulant |
| Furosemide | 98.8 | Loop diuretic |
| Phenylbutazone | 96.1 | NSAID⊕ |
| Valproic Acid | 93.0 | Antiepileptic |

-continued

| Drug | % Albumin Binding | Drug Class |
| --- | --- | --- |
| Sulfisoxazole | 91.4 | Sulfonamide antibiotic |
| Ceftriaxone | 90–95* | Third Generation cephalosporin antibiotic |
| Miconazole | 90.7–93.1* | Antifungal |
| Phenytoin | 89.0 | Antiepileptic |

⊕Nonsteroidal anti inflammatory drug
*Represents patient-to-patient variability

If orosomucoid is added to the dextrose albumin, then the list of drugs which could be potentiated would also include erythromycin (antibiotic), lidocaine (antiarrhythmic), meperidine (analgesic), methadone (analgesic), verapamil and diltiazem (antianginals), cyclosporine (an immunosuppressant), propanolol antihypertensive and antianginal), and quinidine (antiarrhythmic).

Other drugs which bind with albumin, particularly at site 1 would also be useful in this embodiment and can be ascertained by those of skill in the art through drug interaction and pharmacology texts standard to the art such as "Drug Information" AHFS 1994 or "Facts and Comparisons" published by Berney Olin updated every quarter. Assays for determination of appropriate protein-biologic agent combinations are disclosed herein and can be used to test any combination for its ability to work with the method of the invention.

According to one embodiment of the invention, albumin coated microbubbles of perfluorocarbon gas have been found to form stable conjugates with oligonucleotides. The ODN conjugated bubbles are then parenterally introduced to the animal as in traditional ultrasound visualization.

A diagnostic ultrasound field is then introduced when the injected bolus reaches the target site. This can be accomplished in any of a number of ways. For example, the ultrasound transducer can be placed directly above the target site. Thus when the injectate reaches this site it will be exposed to the field and the agent will be released. This method will also allow for visualization as the bolus enters the ultrasound field. The energy provided by the ultrasound will cause the microbubble to release the agent at the therapeutic site or into the blood pool.

Alternatively, the ultrasound transducer can be placed over a site in the blood pool which will permit constant exposure of the microbubbles as they pass through the circulation. The purpose of this is to enhance the systemic effects of certain drugs, such as heparin. Examples of placement sites where this could occur would be over the heart chambers, aorta, or vena cavae. Another method would be to use the contrast agent alone to time the travel from administration to therapeutic site and then inject the biologic conjugated microbubble suspension with application of ultrasound after the appropriate time interval.

This invention is of particular relevance for oligonucleotide and polynucleotide therapy as the primary hurdle to effective anti-sense, anti-gene, probe diagnostics or even gene therapy employing viral or plasmid nucleotide delivery is the ability of the therapeutic to reach the target site at high enough concentrations to achieve a therapeutic effect.

Therapeutic sites can include such things as the location of a specific tumor, location of a specific infection, an organ which due to differential gene activation expresses a particular gene product, the site of an injury or thrombosis, a site for further processing and distribution of the therapeutic etc.

The method preferred for practicing the delivery therapy of the invention involves obtaining a pharmaceutical liquid agent of the invention, and first introducing said agent into a host by intravenous injection, intravenously (i.v. infusion), percutaneously or intramuscularly. The injectate can then be monitored or timed until the target area is reached by the injectate. Low frequency (20 kilohertz to about 2 megahertz) ultrasound is introduced at the target site using a suitable Doppler or ultrasound echo apparatus so that the field of ultrasound encompasses the target site and medicament is released from the microbubble. The ultrasound signal activates the microbubbles so that the microbubble-therapeutic bond is broken and the agent is released at the effective area. The time period will generally vary according to the organ of interest, as well as the injection site. It must only be long enough for some of the agent to have reached the organ of interest.

The desired ultrasound is applied by conventional ultrasonic devices which can supply an ultrasonic signal of 20 Khz to several Mhz and is generally applied from about 3 to about 5 Mhz for diagnostic ultrasound and preferably at levels of less than 1 Mhz, preferably 20 Khz for the therapeutic ultrasound.

Methods of diagnostic ultrasound imaging in which microbubbles, formed by sonicating an aqueous protein solution, are injected into a mammal to alter the acoustic properties of a predetermined area which is then ultrasonically scanned to obtain an image for use in medical procedures is well known. For example see U.S. Pat. Nos. 4,572,203, 4,718,433 and 4,774,958, the contents of each of which are incorporated herein by reference.

It is the use of these types of contrast agents as a pharmaceutical composition and application of ultrasound as a targeted delivery system that is the novel improvement of this invention. The use of a nitrogen-free environment in the manufacture of the contrast agents is also a novel improvement in the effectiveness of the contrast agent in myocardial imaging.

The invention has been shown to drastically improve the efficiency and therapeutic activity of several drugs including most notably anti-sense oligonucleotides which have been traditionally plagued with ineffective pharmacologic parameters, including high clearance rate and toxicity.

The protein substance such as human serum albumin is easily metabolized within the body and excreted outside and hence is not harmful to the human body. Further, gas trapped within the microbubbles is extremely small and is easily dissolved in blood fluid; perfluoropropane and perfluorobutane have long been known to be safe in humans. Both have been used in humans for intra ocular injections to stabilize retinal detachments. Wong and Thompson, ophthalmology 95:609–613. Thus, agents of the invention are extremely safe and nontoxic for patients.

The invention is particularly useful for delivery of nucleotide sequences in the form of gene therapy vectors, diagnostic nucleotide probes, or anti-sense or anti-gene type strategies to ultimately alter or detect gene expression in target cells.

Traditional limitations of oligonucleotide therapy have been preparation of the oligonucleotide analogue which is substantially resistant to the endo- and exonucleases found in the blood and cells of the body. While unmodified ODN's have been shown to be effective, several modifications to these ODN's have helped alleviate this problem.

Modified or related nucleotides of the present invention can include one or more modifications of the nucleic acid bases, sugar moieties, internucleoside phosphate linkages, or combinations of modifications at these sites. The internucleoside phosphate linkages can be phosphorothioate, phosphoroamidite, methylphosphonate, phosphorodithioate and combinations of such similar linkages (to produce mix backbone modified oligonucleotides). Modifications may be internal or at the end(s) of the oligonucleotide molecule and can include additions to the molecule of the internucleoside phosphate linkages, such as cholesterol, diamine compounds with varying numbers of carbon residues between the amino groups, and terminal ribose, deoxyribose and phosphate modifications which cleave, or crosslink to the opposite chains or to associated enzymes or other proteins which bind to the genome. These modifications traditionally help shield the ODN from enzymatic degradation within the cell. Any of the above modifications can be used with the method of the invention. However, in a preferred embodiment the modification is a phosphorothioate oligonucleotide.

Antisense oligonucleotides represent potential tools in research and therapy by virtue of their ability to specifically inhibit synthesis of target proteins. A major theoretical advantage of these ODN's is their potential specificity for binding to one site in the cell. According to one embodiment of the invention a synthetic oligonucleotide of at least 6 nucleotides, preferably complementary to DNA (antigen) or RNA (antisense), which interferes with the process of transcription or translation of endogenous proteins is presented.

Any of the known methods for oligonucleotide synthesis can be used to prepare the oligonucleotides. They are most conveniently prepared using any of the commercially available, automated nucleic acid synthesizers, such as Applied Biosystems, Inc., DNA synthesizer (Model 380B), according to manufacturers protocols using phosphoroamidite chemistry, Applied Biosystems (Foster City, Calif.). Phosphorothioate oligonucleotides were synthesized and purified according to the methods described in Stek and Zon *J. Chromatography*, 326:263–280 and in Applied Biosystems, DNA Synthesizer, User Bulletin, Models 380A-380B-381A-391-EP, December 1989. The ODN is introduced to cells by methods which are known to those of skill in the art. See Iversen, et al., "Anti-Cancer Drug Design", 1991, 6531–6538, incorporated herein by reference.

The following examples are for illustration purposes only and are not intended to limit this invention in any way. It will be appreciated by those of skill in the art, that numerous other protein-bioactive agent combinations can be used in the invention and are even contemplated herein. For example, if the filmogenic protein is alpha-one acid glycoprotein, the bioactive agent could be lidocaine, inderal, or heparin.

In all the following examples, all parts and percentages are by weight unless otherwise specified, all dilutions are by volume.

EXAMPLE 1

Phosphorothioate Oligonucleotide Synthesis

Chain extension syntheses were performed on a 1 $\mu$mole column support on an ABI Model 391 DNA synthesizer (Perkin Elmer, Foster City, Calif.) or provided by Lynx Therapeutics, Inc. (Hayward Calif.). The 1 micromole synthesis employed cyanoethyl phosphoroamidites and sulfurization with tetraethylthiuram disulfide as per ABI user Bulletin 58.

Radiolabeled oligonucleotides were synthesized as hydrogen phosphonate material by Glen Research (Bethesda, Md.). The uniformly $^{35}$S-labeled PS-ODN with sequences 5'-TAT GCT GTG CCG GGG TCT TCG GGC 3' SEQ ID NO:2 (24-mer complementary to c-myb) and 5' TTAGGG 3' SEQ ID NO:3 were incubated in a final volume of 0.5 ml with the perfluorocarbon-exposed sonicated dextrose albumin microbubble solution for 30 minutes at 37° C. The solutions were allowed to stand so that the bubbles could rise to the top and 100 microliters were removed from the clear solution at the bottom and 100 microliters were removed from the top containing the microbubbles. It is to be understood that the method of the invention is nonsequence specific and any base sequence composition of the ODN can be used.

Preparation of Microbubble Agent

Five percent human serum albumin and five percent dextrose were obtained from a commercial source. Three parts of 5% dextrose and one part 5% human serum albumin (total 16 milliliters) were drawn into a 35-milliliter Monojet syringe. Each dextrose albumin sample was hand agitated with 8±2 milliliters of either a fluorocarbon gas (decafluorobutane; molecular weight 238 grams/mole) or 8±2 milliliters of room air, and the sample was then exposed to electromechanical sonication at 20 kilohertz for 80±5 seconds. The mean size of four consecutive samples of the perfluorocarbon-exposed sonicated dextrose albumin (PESDA) microbubbles produced in this manner, as measured with hemocytometry was 4.6±0.4 microns, and mean concentration, as measured by a Coulter counter was 1.4× $10^9$ bubbles/milliliter. The solution of microbubbles was then washed in a 1000 times volume excess of 5% dextrose to remove albumin which was not associated with the microbubbles. The microbubbles were allowed four hours to rise. The lower solution was then removed leaving the washed foam. The washed foam was then mixed with 0.9% sodium chloride.

Binding Assays

The radioactive 24-mer PS-ODN was added to a washed solution of PESDA and room air sonicated dextrose albumin (RA-SDA) microbubbles at a concentration of 5 nM. Nonradioactive PS-ODN 20-mer was added to tubes containing radioactive 24-mer in a series of increasing concentrations (0, 3.3, 10, 32.7, 94.5, 167, and 626 $\mu$M). The suspension of bubbles is mixed by inversion and incubated at 37° C. for 60 minutes.

Measurement of Radioactivity

Radioactivity in solutions was determined by liquid scintillation counting in a liquid scintillation counter (model LSC7500; Beckman Instruments GmbH, Munich, Germany). The sample volume was 100 $\mu$l to which 5 ml of Hydrocount biodegradable scintillation cocktail was added and mixed. Samples were counted immediately after each experiment and then again 24 hours later in order to reduce the influence of chemiluminescence and of quenching.

Flow Cytometry

The uniformity of room air versus perfluorocarbon-containing sonicated dextrose albumin microbubble binding of PS-ODN was determined by flow cytometry. A solution of microbubbles was washed in a 1000 fold excess volume of sterile saline. Three groups of samples were prepared in triplicate as follows; Group A (control) in which 100 $\mu$l of microbubbles were added to 900 $\mu$L of saline, Group B in which 100 $\mu$L of microbubbles were added to 900 $\mu$L of saline and 2 $\mu$L of FITC-labeled 20-mer was added (final 20-mer concentration is 151 nM), and group C in which 100 $\mu$L of microbubbles were added to 800 $\mu$L of saline, 2 $\mu$L of FITC-labeled 20-mer and 100 $\mu$L of unlabeled 20-mer(final concentration is 151 nM). The incubations were all conducted for 20 minutes at room temperature.

Washed microbubble suspensions were diluted in sterile saline (Baxter) and then incubated with FITC-labeled PS-ODN. Flow cytometric analysis was performed using a FACStar Plus (Becton Dickinson) equipped with 100 mW air-cooled argon laser and the Lysis II acquisition and analysis software. List mode data were employed for a minimum of $10^4$ collected microbubbles and independent analysis a for each sample.

Study Protocol

A variable flow microsphere scanning chamber was developed for the study which is similar to that we have described previously Mor-Avi V., et al "Stability of albunex microspheres under ultrasonic irradiation; and in vitro study. *J Am Soc Echocardiogr* 7:S29, 1994. This system consists of a circular scanning chamber connected to a Masterflex flow system(Microgon, Inc., Laguna Hills Calif.) The scanning chamber was enclosed on each side by water-filled chambers and bound on each side by acoustically transparent material. The PS-ODN-labeled PESDA microbubbles (0.1 milliliters) were injected as a bolus over one second proximal to the scanning chamber which then flowed through plastic tubing into a tap water-filled scanning chamber at a controlled flow rate of 100 ml/min. As the bubbles passed through the scanning chamber, the scanner(2.0 Megahertz) frequency, 1.2 Megapascals peak negative pressure) was set to either deliver ultrasound at a conventional 30 Hertz frame rate or was shut off. Following passage through the scanning chamber, the solution was then passed through the same size plastic tubing into a graduated cylinder. The first 10 milliliters was discarded. Following this, the next 10 milliliters was allowed to enter into a collection tube. The collection tube containing the effluent microbubbles was allowed to stand in order to separate microbubbles on the top from whatever free oligonucleotide existed in the lower portion of the sample. Drops from both the upper and lower operation of the effluent were then placed upon a hemocytometer slide and analyzed using a 10x magnification. Photographs of these slides were then made and the number of microbubbles over a 36 square centimeter field were then hand-counted. The upper and lower layers of the remaining effluent were then used for analysis of oligonucleotide content using flow cytometry in the same manner described below.

Microbubble samples exposed to the various oligonucleotide solution were mixed 1:5(v/v) with a solution of formamide and EDTA and heated to 95° C. for 5 minutes. These samples were then examined on an Applied Biosystems Model 373A DNA sequencer with 20% polyacrylamide gel. The data were acquired with GeneScanner software so that fluorescence intensity area under the curve could be determined.

The in vivo studies of the effect of these same diagnostic ultrasound pressures on kidney uptake of PS-ODN were performed in three dogs. Intravenous injections of fluorescent PS-ODN labeled PESDA microbubbles (0.2 ml) were given in the femoral vein in these dogs. The left kidney in each dog was being insonified by an externally placed 2.0–2.5 Megahertz diagnostic ultrasound transducer(peak negative pressure 1.1 MPa). The kidney was insonified using a 30 Hertz frame rate for a minimum of 2 minutes after injection, and during the visually evident appearance of contrast in the kidney. In each dog, left ventricular and pulmonary artery pressures were monitored before and after kidney injection using saline filled catheters placed in the left ventricle and pulmonary artery, respectively. Approximately four hours after injection, the dog was sacrificed and both kidneys removed. Cut sections were then obtained from the renal cortex and sampled for PS-ODN counted using the gene scanning methods described above. Histologic sections were also obtained for the analysis of fluorescence in the glomeruli and nephrons.

Analysis of Data

Statistical analysis of data were obtained using InStat software (GraphPad, San Diego Calif.) with both unpaired t-test for comparison of multiple samples and paired t-tests for comparison of partitioning of PS-ODN from the top to bottom of a sample. Graphical analysis of data were obtained using Prism software (GraphPad, San Diego, Calif.).

Phosphorothioate Oligonucleotide Binding of PESDA Versus RA-SDA Microbubbles

The partitioning of PS-ODN to PESDA microbubbles (top layer) and non-bubble washed (albumin-free) and unwashed (non-bubble albumin containing) lower layers as counted by liquid scintillation counting are demonstrated in Table 1.

TABLE 1

OLIGONUCLEOTIDES BIND TO ALBUMIN OF PESDA MICROBUBBLES

| | N | TOP cpm/µl | BOTTOM cpm/µl | RATIO T/B |
|---|---|---|---|---|
| BUBBLES IN THE PRESENCE OF FREE ALBUMIN | | | | |
| TTAGGG | 6 | 125 ± 6.4 | 92.3 ± 6.4 | 1.35 |
| c-myb | 6 | 94.1 ± 17.6 | 77.3 ± 1.2 | 1.35 |
| WASHED BUBBLES (NO FREE ALBUMIN) | | | | |
| TTAGGG | 6 | 210 ± 10.8 | 126 ± 8.7 | 1.67 |
| c-myb | 6 | 200.3 ± 37.4 | 92.7 ± 15.7 | 2.16 |

These data indicate that albumin in the unwashed solution which is not associated with the microbubble will bind to the PS-ODN so that the partitioning of PS-ODN is equivalent between microbubbles(top layer) and the surrounding solution (lower layer; p=HS). Removal of non-microbubble associated albumin (Washed Bubbles in Table 1) does not show a significant partitioning of the PS-ODNs with the PESDA microbubbles (1.67 for TTAGGG PS-ODN and 2.16 for c-myb PS-ODN). The recovery of total radioactivity in the experiments reported in Table 1 is 96% of the radioactivity added which is not significantly different from 100%.

Figure 1:
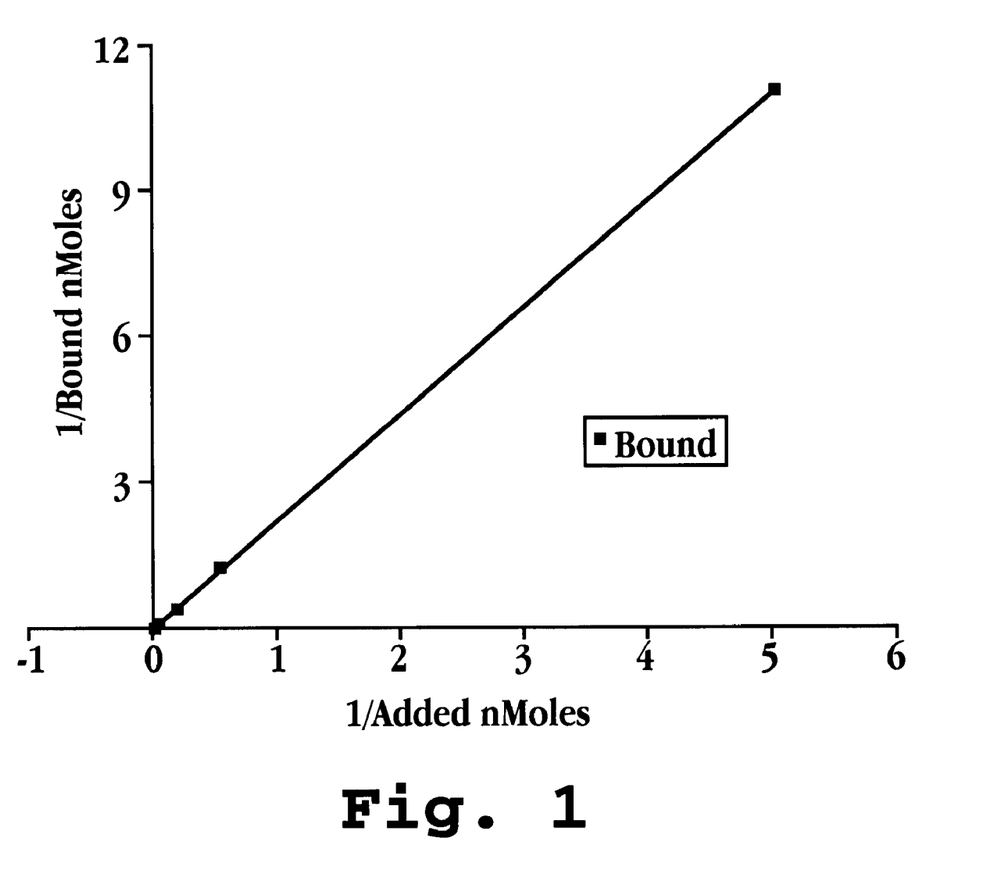

The affinity of binding of PS-ODN to washed microbubbles was evaluated by addition of increasing amounts of excess non-radioactive PS=ODN as a competing ligand for binding sites. In this case a 20 mer PS-ODN with sequence 5'-d(CCC TGC TCC CCC CTG GCT CC)-3' was employed to displace the radioactive 24 mer. Albumin protein concentrations in the washed microbubble experiments was 0.28±0.04 mg/ml as determined by the Bradford Assay, Bradford M et al "A Rapid and Sensitive Method for the quantification of microgram quantities of protein utilizing the principle of protein-dye binding" *Anal. Bioche,.* 72:248, 1976. The observed binding data are presented as a Lineweaver Burke plot in FIG. 1. The equilibrium dissociation constant $K_m$ (calculated for the 7 concentrations which were run in duplicate) for the binding to the microbubbles was $1.76 \times 10^{-5}$ M.

The distribution of FITC-labeled microbubbles is provided in Table 2.

TABLE 2

DISTRIBUTION OF OLIGONUCLEOTIDE
(PS-ODN) BOUND MICROBUBBLES

| No. | Control PS-ODN | | 151 nM FITC PS-ODN | | Excess Unlabeled ODN | |
|---|---|---|---|---|---|---|
| | PE | MI | PE | MI | PE | MI |
| 1 | 99.5 | 2.38 | 98.9 | 2109.8 | 97.8 | 1753.1 |
| 2 | 99.3 | 4.07 | 99.1 | 2142.3 | 98.7 | 1710.9 |
| 3 | 99.4 | 3.52 | 99.1 | 2258.5 | 99.3 | 1832.2 |
| mean ± SE | | 3.23 ± 0.50 | | 2170 ± 46[1] | | 1765 ± 36[1,2] |

PE = percent events
MI = mean intensity
SE = standard error
[1]indicates this mean is significantly different form control, $P < 0.001$
[2]indicates this mean is significantly different form 151 nM, $P < 0.001$ The significant decrease in mean fluorescence intensity in the samples containing excess unlabeled PS-ODN indicates the binding to microbubbles is saturable. Consequently, since the binding is saturable, the nonspecific interactions of PS-ODN with the microbubble surface are limited. The Gaussian distribution of PS-ODN to washed PESDA microbubbles indicated that the albumin on these microbubbles retained its binding site for the oligonucleotide. The absence of a Gaussian distribution for washed RA-SDA indicated that loss of albumin binding site 1 for this oligonucleotide occurred during sonication of these microbubbles. For a discussion of albumin binding characteristics particularly as they relate to oligonucleotides see Kumar, Shashi et al "Characterization of Binding Sites, Extent of Binding, and Drug Interactions of Oligonucleotides with Albumin" Antisense Research and Development 5: 131–139 (1995) the disclosure of which is hereby incorporated by reference.

Influence of Diagnostic Ultrasound on Ps-ODN Bound Microbubbles; In Vitro and In Vivo Observations The observed influence of the 2.0 Megahertz diagnostic ultrasound of PS-ODN-labeled PESDA microbubbles in the suspension is provided in Table 3.

without ultrasound versus 53±21 microbubbles in the top layer of the effluent when exposed to diagnostic ultrasound). This loss of microbubble counts was evident regardless of the PS-ODN concentration attached to the upper bubble containing layer when no ultrasound was applied. In the presence of diagnostic ultrasound, however, the PS-ODN concentration measured by gel electrophoresis in the lower non-bubble containing layer was significantly increased.

In one dog, there was over a 10-fold greater uptake of PS-ODN in the insonified kidney compared to the noninsonified kidney following intravenous PS-ODN in labeled PESDA. In two of the three dogs, this partitioning of PS-ODN uptake to the insonified kidney was evident. In the first dog, there was a 3-fold higher uptake of PS-ODN in the insonified kidney versus the noninsonified kidney. In the second dog, there was over a nine-fold higher uptake of PS-ODN in the insonified kidney. In dog three, however, there was no difference in PS-ODN uptake between the two kidneys. There were no hemodynamic changes following the intravenous injections of PS-ODN-labeled PESDA microbubbles. Histologic examination of the kidneys postmortem also indicated no destruction of any glomerular or tubular cells by the diagnostic ultrasound.

Two important aspects of the invention are herein demonstrated. First, PS-ODN binds to the albumin in PESDA microbubbles, indicating that the binding site 1 on albumin is biologically active following production of these bubbles by electromechanical sonication. This binding site affinity is lost when the electromechanical sonication is performed only with room air. Further, removal of albumin not associated with PESDA microbubbles by washing shows a significant partitioning of the PS-ODNs with the microbubbles (Table 1). These observations demonstrate that albumin denaturation does not occur with perfluorocarbon-containing dextrose albumin solutions during sonication as has been suggested with sonication in the presence of air. The retained bioactivity of albumin (especially at site 1) in PESDA microbubbles was confirmed by the affinity of binding of PS-ODN to washed PESDA microbubbles in the presence of increasing amounts of excess non-radioactive PS-ODN as a competing ligand for binding sites (Table 2). The significant decrease in mean fluorescence intensity in the samples containing excess unlabeled PS-ODN indicates the binding to microbubbles is saturable.

TABLE 3

ANALYSIS OF PS-ODN AND MICROBUBBLE COUNTS AFTER
DIAGNOSTIC ULTRASOUND EXPOSURE TO MICROBUBBLES
Microbubble counts are in parentheses

| | PS-ODN concentration (microbubble Counts) no ultrasound | | | PS-ODN concentration (microbubble Counts) with ultrasound | | |
|---|---|---|---|---|---|---|
| ODN nM | top | bottom | T/B | top | bottom | T/B |
| 0.015 | 189 | 158 | 1.2 | 188 | 187 | 1.0 |
| | (112) | (16) | (7.0) | (56) | (12) | (4.7) |
| 0.1 | 169 | 94 | 1.8 | 184 | 191 | 1.0 |
| | (256) | (8.0) | (8.0) | (16) | (32) | (2.0) |
| 1.0 | 209 | 198 | 1.1 | 254 | 255 | 1.0 |
| | (288) | (8.0) | (36.0) | (88) | (40) | (2.0) |
| Mean ± SE | 203 ± 19 | 147 ± 25 | 1.5 ± 0.2 | 210 ± 18.6 | 219 ± 20.0 | 1.0 ± 0.0 |
| | (219 ± 54) | (19 ± 7) | (17 ± 10) | (53 ± 21) | (20 ± 10) | (3 ± 1.0) | top = top layer of effluent solution after insonification;
bottom = bottom layer of effluent solution after insonification There is a significant loss of microbubbles in the top layer following exposure to ultrasound (219±54 microbubbles Second, exposure of PS-ODN-labeled PESDA microbubbles to diagnostic ultrasound does not alter the integrity of the PS-ODN but does release it from its albumin binding (Table 3).

EXAMPLE 2

In one dog, intravenous heparin in a bolus dose of 1500 units was given in three different settings. Baseline measurements of activated partial thromboplastin time (PTT) were measured and then at five minute intervals after each injection for a minimum of 15 minutes. In setting 1, the heparin was given as the free drug. In setting 2, 1500 units heparin was given bound to orosomucoid PESDA but NO ultrasound was applied to the blood pool. In setting 3, the same dose of heparin (1500 units) bound to orosomucoid PESDA but ultrasound was applied to the blood pool. In setting 1, the PTT increased to >106 seconds at five minutes, but returned to between 30 to 60 seconds at 15 minutes. In setting 2, the PTT did not reach >106 seconds until 10 minutes, but at 15 minutes it was back to between 60 and 80 seconds. In setting 3, the PTT remained >106 seconds even at 15 minutes. No further measurements were made.

EXAMPLE 3

Comparison Study of Microbubbles Formed in Nitrogen-Free Versus Room Air Environments The perfluorocarbon containing microbubbles (PCMB) used for this study were perfluorocarbon exposed sonicated dextrose albumin. To prepare these microbubbles, one part 5% human serum albumin and three parts 5% dextrose (total of 16 ml) were combined in a 35 ml Monoject syringe (Sherwood Medical, St. Louis, Mo.). This sample was then hand-agitated with 8 ml of fluorocarbon gas (decafluorobutane; MW 238 g/mol). Following the agitation, the sample underwent electromechanical sonication for 80±2 seconds.

For in vivo studies, the 80 second sonication process was performed in two different environments: either room air or 100% oxygen (nitrogen-free environment) was blown into interface between the sonicating horn and perfluorocarbon dextrose albumin solution during sonication. Each of the samples prepared in this manner had microbubble size determined with hemocytometry and concentration determined with a Coulter counter (Coulter Electronics, Inc. Hiahleah, Fla.).

In Vitro Scanning Chamber Set Up

The scanning chamber system consisted of a 35 ml cylindrical scanning chamber connected to a peristaltic Masterflex flow system (Microgon, Inc., Laguna Hills, Calif.). Enclosed on both sides of the scanning chamber are cylindrical saline filled chambers, bound by acoustically transparent latex material that is 6.6 microns in thickness (Safeskin, Inc.; Boca Raton, Fla.). Pressure within the scanning chamber during ultrasound exposure was measured wit a pressure transducer placed just proximal to the scanning chamber (model 78304A; Hewlett Packard Co., Andover, Mass.), and averaged 7±3 mm Hg throughout all of the trials.

Two different 2.0 Megahertz ultrasound transducers were used for the in vitro studies (Hewlett Packard 1500; Andover, Mass.; and HDI 3000, Advanced Technology Laboratories, Bothell, Wash.). The peak negative pressure generated by the Hewlett Packard transducer was 1.1 megapascals, while it was 0.9 megapascals for the HDI 3000 scanner. Imaging depth for all studies was 8.2 centimeters, and the focal point for both transducers was 8 centimeters. The frame rate for each transducer was either conventional (30–42 Hertz) or intermittent (1 Hertz). All images from the scanning chamber were recorded on high fidelity videotape.

In Vitro Protocol

Arterial blood during room air inhalation was taken from four dogs and three healthy pigs just prior to sacrifice. In four of the animals, additional arterial blood was obtained after the animal had inhaled 100% oxygen for a minimum of 10 minutes. The blood was collected in 60 ml heparinized syringes, and kept in a warm water bath at 37° C. until injected into the scanning chamber. Immediately before injection of the blood into the scanning chamber, 0.2 ml of PCMB were injected via a stopcock into the 60 ml syringe of blood, and mixed gently by inverting and rolling the syringe by hand.

Once the PCMB were well-mixed with the blood, the tip cap was removed from the syringe, and the syringe was connected to plastic tubing (3.5 mm in diameter) proximal to the Masterflex flow system. At a flow rate of 50 ml/minute, the contrast filled blood flowed from the syringe into the tubing and then into the scanning chamber. Once the chamber was filled, the closed stopcock connecting the scanning chamber to the plastic tubing distal to the chamber was opened, and ultrasound exposure (intermittent at 1 Hertz frame rate or conventional at 30–45 Hertz) was initiated. The effluent blood after ultrasound exposure flowed out of the scanning chamber into tubing which was connected to a graduated cylinder. The first 10 ml of blood was discarded, and the next 15 ml of blood that flowed from the chamber was collected in three 5 ml aliquots into inverted capped syringes. Three minutes following the collection of the last 5 ml sample, a tuberculin syringe was dipped into the top level of the effluent blood and a drop placed on a hemocytometer slide; this length of time was chose to allow the microbubbles in the effluent blood to rise to the top and be collected. The hemocytometer slide was then examined at 40×magnification with a light microscope (Olympus BH-2, Olympus America Inc., Woodbury, N.Y.) and the field containing the highest concentration of microbubbles was photographed on the hemocytometer field.

The photos were later enlarged on a photocopy machine, and a 25 cm$^2$ field was chosen to analyze concentration and the diameter of each microbubble in the field. The mean diameter was calculated, thus giving mean microbubble size. Concentration was determined by counting the total number of bubbles in the entire slide. Microbubble concentration measured with this technique has correlated very closely with Coulter counter measurements, and size measurements with this technique have been calibrated with a known 5 micron sphere (Coulter Size Standards Nominal 5 $\mu$m Microspheres, Miami, Fla.).

In Vivo Studies

The inventors subsequently tested the effect of a nitrogen-free environment within the perfluorocarbon microbubble by randomly giving intravenous injections of PCMB of the same concentration of microbubbles exposed to either 100% oxygen (O2 PCMB) or room air (RA PCMB) during sonication. Imaging was performed with a 1.7 megahertz harmonic transducer (HDI 3000; Advanced Technology Laboratories; Bothell, Wash.). Transducer output was set to 0.3–0.8 megapascals, and kept constant for all comparisons of videointensity from the two different microbubble samples. Frame rates for comparison of background subtracted myocardial videointensity were either 43 Hertz (conventional) or 10 Hertz (intermittent). All procedures were approved by the Institutional Animal Care and Use Committee and was in compliance with the Position of the American Heart Association on Research Animal Use.

The bolus injections of RA PCMB and O2 PCMB were either 0.0025 or 0.005 ml/kg, since the concentrations of each microbubble were the same. Peak anterior and posterior myocardial videointensity were measured from digitized super VHS videotape images (Maxell, Japan) obtained off-line using a Tom-Tech review station (Louisville, Colo.). This quantifies videointensity over a 1–255 gray scale range. The region of interest was placed in the mid myocardium of each segment.

In addition to this quantitative analysis, the visual assessment of regional myocardial contrast enhancement in the anterior, septal, lateral, and posterior regions from the short axis view was made by two independent reviewers. Each region was assigned a 0 (no myocardial contrast), 1+(mild myocardial contrast enhancement) or 2+(bright myocardial contrast enhancement which approached cavity intensity).

Statistical Analysis

An unpaired t test was used to compare microbubble size and concentration of the PCMB samples exposed to different gases during sonications. This was also used to compare differences in peak myocardial videointensity in the in vivo studies. If the data was not normally distributed, a non-parametric test was performed. Comparisons of visual myocardial contrast enhancement following intravenous O2 PCMB and RA PCMB were made with continency tables (Fisher's Exact Test). A p value less than 0.05 was considered significant.

A coefficient of variation was used to measure interobserver variability in the measurements of microbubble size and concentration in the in vitro studies. A mean difference between independent reviewers was used to compare interobserver variations in peak myocardial videointensity.

Results

Table 4 demonstrates differences in mean microbubble size for PCMB after exposure to ultrasound in arterial blood (room air and 100% oxygen). When PCMB were exposed to 100% oxygenated arterial blood, there was a significant decrease in mean microbubble size after insonation ($p=0.01$). The smaller microbubble size was seen both after intermittent imaging (7.3±3.7 microns room air vs. 6.4±3.2 microns 100% oxygen) and after conventional imaging (7.5±3.5 microns room air vs. 6.3±3.0 microns 100% oxygen)

TABLE 4

COMPARISON OF EFFLUENT PESDA MICROBUBBLE SIZE AFTER EXPOSURE TO DIFFERENT ULTRASOUND FRAME RATES IN ROOM AIR AND 100% OXYGENATED ARTERIAL BLOOD

|  | MB size ($\mu$m) | MB Conc. (No./hpf) | |
|---|---|---|---|
|  |  | Conv | Inter |
| Arterial | 7.4 ± 3.6 | 6 ± 8 | 16 ± 11† |
| Arterial + $O_2$ | 6.3 ± 3.1 | 11 ± 9 | 14 ± 9* |

Conv = Conventional frame rates (80 to 43 Hz)
No./hpf = Number of microbubbles per high-power field
MB = microbubble
Inter = Intermittent imaging at 1 Hz
*p < 0.05 r test compared with arterial samples
†p < 0.05 compared with arterial conv.

Microbubble concentration decreased significantly after exposure to conventional frame rates when compared to intermittent imaging in room air arterial blood (Table 4). However, conventional frame rates at the same transducer output did not destroy as many PCMB when they were in oxygenated arterial blood.

In Vivo Studies

A total of six comparisons of peak myocardial videointensity between O2 PCMB and RA PCMB were made in the three dogs. In Table 5, it can be seen that prior to injection, the PCMB sonicated in the presence of 100% oxygen were similar in size and concentration to PCMB sonicated in the presence of room air. However, in all three dogs, the peak myocardial videointensity using the 10 Hertz frame rate (intermittent imaging) was significantly higher for the PCMB sonicated in the presence of 100% oxygen.

TABLE 5

COMPARISON OF PMVI PRODUCED IN ANTERIOR AND POSTERIOR WALL OF LEFT VENTRICULAR SHORT-AXIS VIEW AT MID PAPILLARY MUSCLE LEVEL AFTER INTRAVENOUS VEIN INJECTION OF PCMB SONICATED IN THE PRESENCE OF 100% OXYGEN AND ROOM AIR

|  | PMVI (units) | | Microbubble | |
|---|---|---|---|---|
|  | Ant | Post | Size ($\mu$m) | Conc (No./hpf) |
| RA PCMB | 54 ± 12 | 19 ± 9 | 4.0 ± 2.4 | 109 ± 30 |
| $O_2$ PCMB | 70 ± 6* | 31 ± 5* | 3.9 ± 2.3 | 108 ± 50 |

Ant = anterior myocardium
Conc = microbubble concentration immediately after sonication
$O_2$ PCMB = perfluorocarbon microbubbles sonicated in the presence of 100% oxygen
PMVI = peak myocardial videointensity
Post = posterior myocardium
RA PCMB = perfluorocarbon microbubbles sonicated in the presence of room air
No./hpf = number of microbubbles per high-power field
*p < 0.05 compared with RA PCMB Only with the oxygenated PCMB produced a consistent homogenous myocardial contrast at the doses used for transthoracic imaging. Visual myocardial contrast was 2+ in 20 of the 24 regions following intravenous $O_2$ PCMB injections compared to 9 or 24 regions following the same dose of RA PCMB ($p=0.001$).

Interobserver Variability in Microbubble Size, Concentration, and Videointesity Measurements Two independent observers measured microbubble size and concentration of six different slides exposed to either intermittent or conventional ultrasound frame rates. The coefficient of variation for measurements of microbubble size by two independent observers in six different samples was 8% ($r=0.95$; $p=0.004$), while the coefficient of variation for independent measurements of microbubble concentration was 9% ($r=0.99$; $p<0.001$). The reported mean difference in peak myocardial videointensity measurements by two independent reviewers for transthoracic imaging is 4±4 units ($r=0.94$, SEE=5 units; $p<0.001$; $n=24$ comparisons), which is well below the 16 unit mean difference in anterior and 13 unit mean difference in posterior peak myocardial videointensity between O2 PCMB and RA PCMB. The two investigators were in agreement of the visual degree of contrast enhancement in 37 of the 44 regions (84%). Five of the discrepancies were in visual grading of RA PCMB myocardial contrast enhancement (0 vs 1+ in two regions, 1+ vs. 2+ in three regions). The three regions where there was disagreement on whether there was 1+ vs 2+ were assigned a 2+ in the statistical analysis.

Microbubbles containing an albumin shell such as the one used in this study permit rapid diffusion of soluble gases across their membranes. Perfluorocarbon containing microbubbles survive longer than room air containing microbubbles with the same membrane because of the slow rate of diffusion of this higher molecular weight gas and its insolubility in blood. These microbubbles, however, still contain a significant quantity of room air gas and thus are not affected by the concentration gradient that exists across the albumin membrane. Since surface tension and absorptive pressures are increased as microbubble diameter decreases, it was hypothesized that the videointensity produced by intravenous PCMB would also be affected by alterations in nitrogen and oxygen concentration inside and outside the microbubble.

The in vitro studies confirmed that oxygenated blood reduced PCMB size but did not completely destroy them as has been shown with pure room air containing albumin microbubbles. Wible J. Jr., et al. (1993), Effects of inspired gas on the efficacy of Albunex® in dogs. Circulation 88(suppl):1–401. Abstract. To counter this process, the inventors attempted to reverse this diffusion gradient by removing nitrogen within the microbubbles. It was hypothesized that this would have the opposite effect of that seen with oxygenated blood, resulting in nitrogen diffusion inward. The in vitro and in vivo findings of this study appear to support this hypothesis.

PESDA Microbubble Concentration and Size in Arterial Blood: In Vitro Studies

It has previously been shown that PCMB diameter increases after initial exposure to blood at 37° C., most likely from gas expansion from room temperature to body temperature. Although this explains why microbubble size increased in all samples tested, the PCMB exposed to 100% oxygenated arterial blood were significantly smaller in size compared to PCMB exposed to room air blood (Table 4). This observation was seen both following intermittent and conventional imaging. One potential explanation for this is the differences in nitrogen diffusion gradients across the microbubble membrane. Since all PCMB in the in vitro study were sonicated in the presence of room air, there was a significant quantity of nitrogen within the microbubble. Mathematical models have suggested that microbubbles containing insoluble gases persist longer if tissue and blood contain nitrogen. (Burkard 1994). In the absence of blood nitrogen (i.e.: 100% oxygenated blood), nitrogen from within the PCMB would have diffused out of the PCMB, reducing their size.

As expected, microbubble concentrations in room air blood were significantly reduced when exposed to higher frame rates. However, this destruction by more rapid frame rates was attenuated somewhat when the PCMB were in oxygenated blood. The reason for this difference is unclear. One possibility is that the more rapid diffusion of nitrogen out of the microbubbles in oxygenated blood created a higher internal concentration of perfluorocarbon, and thus increased the diffusion gradient for the insoluble perfluorocarbon. Due to its low solubility, its enhanced diffusion out of the microbubble would lead to the formation of smaller unencapsulated perfluorocarbon microbubbles. The hemocytometry resolution would be unable to differentiate encapsulated from unencapsulated microbubbles and thus would count them both. This explanation may also account for the smaller mean microbubble size observed for PCMB expos ed to 100% oxygenated arterial blood.

PCMB Sonicated in a Nitrogen-Free Environment: In Vivo Demonstration of Improved Efficacy over PCMB Sonicated in the Presence of Room Air Based on the in vitro studies, whether the detrimental effects of a high external oxygen content could be utilized to an advantage by lowering nitrogen content within the PCMB was examined. This was accomplished in our study by sonicating the PCMB in the presence of 100% oxygen. Since perfluorocarbons like decafluorobutane act as a mechanical stabilizer, it was hypothesized that this would create an environment where nitrogen diffuses inward following venous injection, further enhancing the stability of the PCMB in blood. This was consistently effective in the closed chest studies in creating greater myocardial contrast than PCMB sonicated in the presence of room air. Even with intermittent imaging using pulsing intervals as short as 100 milliseconds (10 Hertz imaging), visually evident myocardial contrast was still achieved with the microbubbles sonicated in an oxygen-free environment.

EXAMPLE 4

Inhibition of Carotid Artery Neointimal Formation using Transcutaneous Ultrasound and an Intravenous Microbubble Delivery System Containing Antisense to the c-myc Protooncogene Several investigators have shown that neointimal hyperplasia occurs after vascular balloon injury as a result of smooth muscle cell migration and proliferation (Austin G E, Ratliff N B, Hollman J, Tabei S, Phillips D F. Intimal proliferation of smooth muscle cells as an explanation for recurrent coronary artery stenosis after percutaneous transluminal coronary angioplasty. *J Am Coll Cardiol* 1985;6:369–75; Libby P, Schwartz E, Brogi H, Tanaka H, Clinton S K. A cascade model for restenosis: a special case of atherosclerosis progression. *Circulation* 1992;86:III47–III52; Clowes A W, Clowes M M, Fingerle J, Reidy M A. Regulation of smooth muscle cell growth in injured artery. *J Cardiovasc Pharmacol* 1989;14:S12–S15). This neointimal formation plays a role in the angiographic observation of restenosis after both balloon injury and intravascular stenting (Mintz G S, Kent K M, Pichard A D, Popma J J, Satler L F, Leon M B, Intravascular ultrasound insights into mechanisms of stenosis formation and restenosis, *Cardiol-Clin* 1997;15(1):17–29). Synthetic antisense oligodeoxynucleotides (ODN) that inhibit synthesis of the protooncogenes responsible for vascular smooth muscle proliferation have successfully inhibited stenosis formation following coronary or carotid injury (Shi Y, Fard A, Galeo A, Hutchinson H G, Vermani P, Dodge G r, Hal D J, Shaheen F, Zalewski A, Transcatheter delivery of c-myc antisense oligomers reduces neointimal formation in a porcine model of coronary artery balloon injury, *Circulation* 1994;90:944–51; Morishita R, Gibbons G H, Ellison K E, Nakajima M, von der Leyen H, Zhang L, Kaneda Y, Ogihara T, Dzau V J, Intimal hyperplasia after vascular injury is inhibited by antisense cdk 2 kinase oligonucleotides, *J Clin Invest* 1994;93:1458–1464). To this point, such treatment has required direct intravascular or periadventitial delivery. Recently, we have demonstrated that ODN (to c-myc and c-myb) bind to perfluorocarbon exposed sonicated dextrose albumin (PESDA) microbubbles (Porter T R, Iversen P L, Li S, Xie F. Interaction of diagnostic ultrasound with synthetic oligonucleotide-labeled perfluorocarbon-exposed sonicated dextrose microbubbles, *J Ultrasound Med* 1996;15:577–584). Subsequent observations have shown that transcutaneous low frequency ultrasound increases the deposition of the ODN into vessels contained within the field of insonification (Porter T R, Li S, Iversen P L, The effect of microbubble gas composition and external ultrasound frequency on the non-invasive enhancement of antisense oligonucleotide delivery to the vascular wall in pigs, *Circulation Suppl* 1997;2249). The purpose of this study was to determine whether this enhanced vascular deposition with low frequency ultrasound and intravenously injected ODN to c-myc bound to PESDA microbubbles could inhibit neointimal formation following balloon injury of the carotid artery.

All procedures were approved by the Institutional Animal Care and Use Committee and were in compliance with the Position of the American Heart Association on Research Animal Use. Twenty eight domestic pigs were premedicated with aspirin (325 mg PO). General anesthesia was then obtained with ketamine (20 mg/kg), xylazine (4 mg/kg) and supplemental pentobarbitol. The pigs were intubated and placed on a respirator breathing room air. A Swan Ganz catheter was advanced into the pulmonary artery to monitor pulmonary pressure. Intravenous heparin (4,000–5,000 units), atropine (0.5–1.0 mg), and sublingual nifedipine (10–30 mg) were given. An 8F guide catheter was placed into the proximal portion of the right carotid artery. The artery was injured by dilating the vessel with an oversized balloon (6.0 mm to 10.5 mm) for a mean of 107±34 seconds (range 90–240 seconds). The intervention was performed by an experienced interventional cardiologist (U.D.) who had no knowledge of which treatment the pig was to subsequently receive. Vessel patency following injury was confirmed angiographically with intracarotid injections of Hexabrix or Renographin-76.

The first 20 animals were randomized to receive one of three treatments following balloon injury: (a) intravenous phosphorothioate ODN to c-myc (0.5 milligrams; Lynx Therapeutics; Hayward, Calif.) bound to PESDA (ODN-PESDA); (b) the same dose of intravenous antisense to the c-myc alone (ODN alone); or (c) no injections (control). Injections were repeated on day three following balloon injury in ODN-PESDA and ODN alone pigs. All animals received Ketorolac (60 mg) and Solumedrol (40 mg) intravenously to prevent pulmonary hypertensive responses in those pigs randomized to receive microbubbles. The last eight pigs received a different ODN to c-myc (Morpholine; AVI Biopharma, Inc; Corvallis, Oreg.). In these pigs, the first four were to receive ODN bound to PESDA, and the last four received either ODN alone (n=2) or no treatment (n=2) following balloon injury.

In those randomized to ODN-PESDA, a transcutaneous 20 kilohertz ultrasound probe (Model XL2020; Heat Systems; Farmingdale, N.Y.) at a power output of 50 Watts/cm$^2$ insonified the region over the right carotid artery before and after each injection for a total of six minutes both immediately after balloon dilatation and on day three. To avoid skin irritation due to probe heating, a 1.5–2.0 centimeter coupling gel was placed between the skin surface and the probe tip using an inverted cut-off 12 milliliter syringe. The right carotid artery location was confirmed with a diagnostic transducer (HDI3000; Advanced Technology Laboratory; Bothell, Wash.).

Measurements at 30 days Following Balloon Injury

At 30 days following balloon injury, intravascular ultrasound (IVUS) measurements were made prior to sacrificing the pig. A 2.9 or 3.1 F 30 Megahertz IVUS catheter (CVIS; Sunnyvale, Calif.) was advanced under fluoroscopy into the distal carotid artery and a motorized pullback of the catheter was performed. Off line planimetry of lumen area, total vessel area (lumen plus any visualized plaque), and vessel diameter was performed at the site of greatest plaque and smallest lumen in the previously injured area. The pigs were then sacrificed, and serial sections of the carotid artery performed after fixation. The site of maximal intimal thickness was measured by digital planimetry (NIH Image 1.61; Bethesda, Md.). Since the vessels did not undergo perfusion fixation, the value for maximal intimal thickness was indexed to vessel diameter at the balloon injury site measured by IVUS. Both IVUS and histologic measurements were made by reviewers (W. H. and S. R, respectively) who had no knowledge of which treatment regimen the pig received.

Statistical Analysis

Differences in IVUS measurements of total vessel area, lumen area, and lumen diameter at the balloon injury sites and histologic measures of maximal intimal thickness in the three groups were compared using analysis of variance (Student-Newmann-Keuls multiple comparison procedures). Since IVUS could not be performed in three pigs receiving ODN alone, data from ODN alone and control were also combined and compared with ODN-PESDA by Student's t-test or Mann-Whitney Rank Sum test. Intraobserver variability in IVUS and histologic measurements were computed by having the same reviewer repeat measurements at different times and compute the percent difference between measurements.

Results

Two pigs died during the balloon injury protocol. In five pigs, (three in ODN-PESDA, one in IV ODN alone, and one control) there was no histologic evidence of injury or intimal hyperplasia at 30 days following injury. Of the remaining 21 pigs, eight received ODN-PESDA, seven received intravenous ODN alone, and six received nothing. The pigs treated with 20 kilohertz ultrasound had a superficial abrasion at the site of applied ultrasound which was no longer evident at 30 days follow-up.

Table 1 contains the intravascular ultrasound and histologic data in the three groups. Intravascular ultrasound was possible in 16 of the pigs. It could not be performed in three of the pigs that received ODN alone because of thrombotic occlusion at 30 days following injury, and in one each of the pigs that received ODN-PESDA and ODN alone for technical reasons. Both total vessel area and lumen area at the injury site measured with IVUS were significantly larger in the ODN-PESDA group. This larger vessel size was seen despite significantly smaller maximal intimal thickness in this same group at histology. When histologic measures of maximal intimal thickness were indexed to IVUS vessel diameter, there was a clear cut distinction between the three groups (Table 1).

The control pig had a smaller vessel but greater intimal thickness at 30 days when compared to the pig treated with ultrasound and ODN-PESDA. Intraobserver variability was 3% (n=12 comparisons) in IVUS measurements, and 14% (n=25 comparisons) for repeated histologic measurements.

The methods of ODN delivery following arterial injury in previous studies have required either direct intraarterial delivery or periadventitial application (5,6,9 Shi Y, Fard A, Galeo A, Hutchinson H G, Vermani P, Dodge G r, Hal D J, Shaheen F, Zalewski A, Transcatheter delivery of c-myc antisense oligomers reduces neointimal formation in a porcine model of coronary artery balloon injury, *Circulation* 1994;90:944–51; Morishita R, Gibbons G H, Ellison K E, Nakajima M, von der Leyen H, Zhang L, Kaneda Y, Ogihara T, Dzau V J, Intimal hyperplasia after vascular injury is inhibited by antisense cdk 2 kinase oligonucleotides, *J Clin Invest* 1994;93:1458–1464; Bennett M R, Lindner V, DeBlois D, Reidy M A, Schwartz S M, Effect of phosphorothioated oligonucleotides on neointimal formation in the rat carotid artery, *Arterioscler Thromb Vasc Biol* 1997;17:2326–2332). In our study, we were able to demonstrate that ultrasound-targeted deposition of intravenously administered ODN bound to PESDA microbubbles can also inhibit stenosis formation by both inhibiting intimal hyperplasia as well as creating a significantly smaller intimal thickness to lumen diameter ratio.

In addition to being non-invasive, the ultrasound targeted approach is advantageous because it can be repeated at various time intervals following injury. Periadventitial application of antisense to c-myc has suppressed medial replication, but this suppression is no longer evident at four days following carotid injury in rats (Bennett M R, Lindner V, DeBlois D, Reidy M A, Schwartz S M, Effect of phosphorothioated oligonucleotides on neointimal formation in the rat carotid artery, *Arterioscler Thromb Vasc Biol* 1997;17:2326–2332). Therefore, we chose in this study to give a second 0.5 milligram dose of ODN bound to PESDA intravenously three days following injury.

We observed both decreased intimal hyperplasia and a larger vessel lumen at 30 days in the ODN-PESDA group. It is unknown whether the larger lumen size was due to vessel growth in the ODN-PESDA group or shrinkage in the control groups, since we did not have pre-balloon injury IVUS data. Vessel enlargement has been shown to be a critical factor in determining the degree of stenosis formation following balloon injury, and even more important than the amount of intimal hyperplasia that occurs (Kakuta T, Currier J W, Haudenschild C C, Ryan T J, Faxon D P, Differences in compensatory vessel enlargement, not intimal formation, account for restenosis after angioplasty in the hypercholesterolemic rabbit model, *Circulation* 1994;89:2809–15). The larger lumen area in those treated with ultrasound targeted delivery may indicate that an important effect of ODN to c-myc is to prevent inadequate compensatory enlargement in response to atherosclerosis. One way ODN could produce lumen enlargement is by preventing c-myc-mediated cell migration out of the media, a process that has been inhibited by direct application of the antisense to c-myc (Bennett M R, Lindner V, DeBlois D, Reidy M A, Schwartz S M, Effect of phosphorothioated oligonucleotides on neointimal formation in the rat carotid artery, *Arterioscler Thromb Vasc Biol* 1997;17:2326–2332; Biro S, Fu Y-M, Yu Z-X, Epstein S E, Inhibitory effects of antisense oligonucleotides targeting c-myc mRNA on smooth muscle cell proliferation and migration, *Proc Natl Acad Sci. USA* 1993;90:654–58). Another mechanism whereby ODN could alter vessel size is by inhibiting c-myc's ability to stimulate endothelin-1 production, a potent vasoconstrictor and mitogenic substance (Shichiri M, Adachi S, Sedivy J M, Marumo F, Hirata Y, Biphasic regulation of the preproendothelin-1 gene by c-myc, *Endocrinology* 1997;138(11):4584–90).

This is the first demonstration of the physiologic effectiveness of ultrasound and microbubbles as a delivery system. This study confirms that the enhanced uptake of ODN bound to PESDA microbubbles in the presence of ultrasound has an important effect on stenosis formation following carotid balloon injury.

Ultrasound has been shown to enhance gene expression in cultured HeLa cells when the oligonucleotides are delivered on other carrier systems like cationic liposomes (Unger E C, McCreery T P, Sweitzer R H, Ultrasound enhances gene expression of liposomal transfection, *Invest Radiol* 1997;32:723–27). The mechanism for this enhanced cellular uptake in the presence of ultrasound has been postulated to be cavitation-induced bilayer disordering of the cell membrane (Mitragotri S, Blankschtein D, Langer R, Transdermal drug delivery using low-frequency sonophoresis, *Pharmaceutical Research* 1996;13:411–20). Therefore, microbubbles may have an inherent advantage over other carrier systems by virtue of their ability to lower this cavitation threshold (Holland C K, Apfel R E, Thresholds for transient cavitation produced by pulsed ultrasound in a controlled nuclei environment *J Acoust Soc Am* 1990; 88: 2059–69). If cavitation is the mechanism for enhanced uptake of ODN, both the presence of microbubbles and the lower frequency of ultrasound used in this study (20 kilohertz) may have improved uptake.

In conclusion, intravenous ODN-PESDA and transcutaneous low frequency ultrasound inhibit carotid stenosis formation in a manner similar to direct application of antisense to the vessel wall following balloon injury. These data demonstrate that ultrasound and a microbubble delivery system containing ODN may be a powerful, non-invasive, method to inhibit stenosis formation following balloon angioplasty or intravascular stenting.

TABLE 1

Intravascular ultrasound (IVUS) and histology findings 30 days following carotid balloon injury in pigs receiving either intravenous ODN-PESDA with transcutaneous ultrasound, ODN alone, or nothing (control). MIT = maximal intimal thickness (histology); MIT Index = MIT indexed to vessel diameter (IVUS); LA = lumen area (IVUS); TVA = total vessel area (IVUS). *p < 0.05 compared to ODN alone, [+]p = 0.01 compared to ODN alone and control combined, [#]p < 0.05 compared to all other groups.

|  | MIT (mm) | MIT Index | LA (mm$^2$) | TVA (mm$^2$) |
| --- | --- | --- | --- | --- |
| ODN-PESDA | 0.14 ± 0.04* | 0.58 ± 0.22[+] | 21 ± 3[#] | 24 ± 4[#] |
| ODN alone | 0.41 ± 0.34 | 1.26 ± 0.45 | 13 ± 5 | 15 ± 4 |
| Control | 0.22 ± 0.09 | 1.66 ± 0.86 | 13 ± 6 | 15 ± 5 |

All references cited herein are hereby expressly incorporated by reference.

What is claimed is:

1. A method of inhibiting carotid or coronary artery stenosis formation, comprising:

intravenously administering to an animal a suspension of human serum albumin encapsulated perfluorocarbon gas-filled microbubbles, said microbubbles conjugated to an antisense olioodeoxynucleotide to c-myc, wherein the gas filling the microbubbles has a decreased partial pressure of nitrogen compared to that of microbubbles formed by room air sonication, and exposing the carotid or coronary artery of said animal to ultrasound so that said antisense oligodeoxvnucieotide to c-myc is released at said carotid or coronary artery, such that said antisense oligodeoxynucleotide to c-myc inhibits the expression of endogenous c-myc, thereby inhibiting stenosis formation in said carotid or coronary artery of said animal.

2. The method of claim 1, wherein said microbubbles are formed by sonication in a nitrogen free environment.

3. The method of claim 2, wherein said environment is 100% oxygen.

4. The method of claim 1 wherein said microbubbles are formed by the steps of:

mixing an aqueous solution comprising about 2% to about 10% by weight of human serum albumin diluted about two-fold to about eight-fold with 5% to 50% by weight of dextrose; and exposing said solution to a sonication horn in a nitrogen-free environment to create cavitation at particulate sites in said solution thereby generating stable microbubbles from about 0.1 to 10 microns in diameter.

5. The method of claim 4, wherein the solution is exposed to a nitrogen-free environment comprising 100% oxygen.

6. The method of claim 5, wherein the 100% oxygen is blown into interface between the sonicating horn and the solution.

* * * * *